United States Patent [19]

Jacobs et al.

[11] Patent Number: 4,842,862

[45] Date of Patent: Jun. 27, 1989

[54] IMMUNOSTIMULATING AGENTS

[75] Inventors: Martin J. Jacobs; Carl K. Edwards, III; Paula Myers-Keith, all of Terre Haute, Ind.

[73] Assignee: International Minerals & Chemical Corp., Terre Haute, Ind.

[21] Appl. No.: 881,926

[22] Filed: Jul. 3, 1986

[51] Int. Cl.$^4$ .................. A61F 13/00; A61K 39/00
[52] U.S. Cl. .................................. 424/422; 424/88; 424/89; 424/92; 424/434; 424/435; 424/439; 424/442; 424/451; 424/464
[58] Field of Search ............. 424/422, 464, 434, 451, 424/435, 88, 89, 97, 439, 438, 442

[56] References Cited

U.S. PATENT DOCUMENTS

| | | | |
|---|---|---|---|
| 3,239,341 | 3/1966 | Hodge et al. | 99/2 |
| 3,993,775 | 11/1976 | Williams | 514/885 X |
| 4,173,641 | 11/1979 | Kraska | 424/267 |
| 4,281,120 | 7/1981 | Herrling | 544/117 |
| 4,335,250 | 6/1982 | Umezawa et al. | 514/885 X |
| 4,420,481 | 12/1983 | Okazaki et al. | 424/250 |
| 4,442,031 | 4/1984 | Felix et al. | 260/112.5 R |
| 4,444,767 | 4/1984 | Torelli et al. | 424/238 |
| 4,559,362 | 12/1985 | Umezawa et al. | 514/674 |
| 4,681,760 | 7/1987 | Fathman | 424/85 |

OTHER PUBLICATIONS

Gangadharam, et al., "Release of Superoxide Anion from Resident and Activated Mouse Peritoneal Macrophages Infected with Mycobacterium Intracellulare", Am. Rev. Respir. Dis. 1984; 130: 834-38.

Dyer et al., "Production of Superoxide Anion by Bovine Pulmonary Macrophages . . . " Am. J. Vet. Res., vol. 46, No. 2, pp. 336-341 (Feb. 1985).

Johnston et al., "Increased Superoxide Production by Immunologically Activated and Chemically Elicited Macrophages" J. Exp. Med., pp. 115-127 (1978).

Adams et al., "The Cell Biology of Macrophage Activation" Ann. Rev. Immunol., vol. 12, pp. 283-318 (1984).

Primary Examiner—Thurman K. Page
Attorney, Agent, or Firm—Wendell Ray Guffey; Thomas L. Farquer

[57] ABSTRACT

The Resorcylic Acid Lactone (RAL) derivatives zearalenone, zearalanone, zearalene, zearalane, zearalenol, zearalanol, and dideoxyzearalane are administered to vertebrates to non-specifically stimulate the immune system.

18 Claims, No Drawings

IMMUNOSTIMULATING AGENTS

This invention relates generally to immunostimulating agents and, in particular, to the use of Resorcylic Acid Lactone (RAL) derivatives as immunostimulating agents.

BACKGROUND OF THE INVENTION

The vertebrate immune system is unique in that it is a spread out series of cells and tissue, instead of a concentrated single organ. In humans, there are about $10^{12}$ total cells in the system, including those of the spleen, liver, thymus, bone marrow, lymph nodes, and the circulating cells of the blood and lymph. Together, the cells have a mass of about 2 kilograms, which is about equivalent to that of an adult liver.

In general, the immune system protects an organism from disease by responding to disease causing antigens using a complicated mechanism which recognizes, inactivates, and destroys the antigen. To be effective, the immune system must first discriminate between potential antigens which are the molecules of the organism it serves to protect and actual antigens which are foreign invaders. The immune system must localize and destroy the foreign antigens, a process that involves not only antibodies and lymphocytes but also several plasma proteins that together form a defense mechanism called the complement system.

Interaction of the foreign antigens with components of the immune and complement systems stimulates the production of biologically active substances that amplify immunological recognition. These substances enhance local vascular permeability and vascular stasis and chemotactically attract phagocytic circulatory cells to the local sites of the immune reactions. These processes produce a localized inflammatory response and the recruited cells ingest the antigens.

The immune system, having interacted with a particular antigen, acquires an "immunity" to that specific antigen. Subsequent contact with the same antigen elicits a rapid stimulation of the immune system which quickly destroys the antigen before it can harm the organism. This "immunity" for a specific antigen can be produced by accidental contact with an antigen or can be induced by exposing the immune system to non-lethal doses of the antigen, components of an antigen, or to biologically inactive antigens.

The limitation inherent in the immune system is, however, its specificity. The immune system retains an "immunity" only for the specific antigens with which it has previously reacted. When the immune system first encounters a different antigen, it cannot respond as rapidly to the new invader as it could to a previously encountered antigen for which an immunity had been acquired. This leaves the organism succeptable to disease and other harmful effects caused by new invading antigens even though the immune system has an "immunity" against thousands of other specific antigens. The immune system, because of its specificity, has no method for acquiring an "immunity" against antigens as a general class. A method is therefore needed which can stimulate the immune system non-specifically and produce an effective "immunity" to antigens in general. The immune system could, therefore, rapidly destroy any antigen invading the organism. Such a method would enhance the immune system's ability to combat disease and increase the overall effectiveness of the vertebrate immune system.

Prior art methods for stimulating the immune system include: U.S. Pat. No. 4,420,481 to Okazaki et al discloses the use of piperazine compounds as immunostimulating agents for the treatment of arthritis and other immune system diseases. U.S. Pat. No. 4,281,120 to Herrling discloses using derivatives having immune stimulating properties for anti-infectious therapy in mammals, including man. U.S. Pat. No. 4,173,641 to Kraska discloses glycerol derivatives useful as non-specific stimulants of cell mediated immunity. U.S. Pat. No. 4,444,767 to Torelli et al discloses the use of 3-amino-pregen-5-ene derivatives as stimulants of the mammalian immune system. U.S. Pat. No. 4,571,336 to Houck et al discloses immunostimulating peptides useful for treating mammals and birds at risk from viral or fungal infections or other trauma.

Preparation of the immunostimulating RAL derivatives of the present invention, zearalenone, zearalanone, zearalene, zearalane, zearalenol, zearalanol, and dideoxyzearalane, are disclosed in U.S. Pat. Nos. 3,196,019, 3,239,354, 3,239,341, 3,239,348, 3,239,345, and 3,453,367, all incorporated herein by reference. Some of these compounds are used as growth promotants in animals.

SUMMARY OF THE INVENTION

It is, therefore, an object of the present invention to provide a method for non-specifically stimulating the vertebrate immune system.

It is another object of the present invention to provide a composition for non-specifically stimulating the vertebrate immune system.

It is another object of the present invention to provide a method for increasing vertebrate resistance to antigens such as disease causing organisms and pathogens.

It is another object of the present invention to provide a method for vaccinating a vertebrate against disease causing pathogens.

It is another object of the present invention to provide an adjuvant to be used in conjunction with conventional vaccines.

These and other objects are achieved by administering immunostimulating amounts of the RAL derivatives zearalenone, zearalanone, zearalene, zearalane, zearalenol, zearalanol, and dideoxyzearalane to the vertebrate. Preferably the compounds are administered alone or in combination in dosages from about 1-20 mg/kg of body weight prior to an anticipated infection, stress, or trauma to prevent or mitigate against the clinical manifestations of the resulting disease, although the compounds can be administered after the clinical manifestations occurs to aid the immune system in fighting the disease. The RAL derivatives according to the present invention shorten the time and increase the level of response to the invading antigens thereby providing an effective "immunity" against new antigens invading the organism.

In the preferred embodiment, zearalane is administered to the vertebrate in dosages from about 1-20 mg/kg of body weight to stimulate the immune system and make the vertebrate more resistant to antigen induced infections or diseases caused by stress or other trauma. Preferably zearalane is injected prior to an anticipated infection, stress, or trauma to prevent the resulting disease, although the compound can be administered after the disease occurs to aid the immune system in fighting the disease.

Other objects, advantages, and novel features of the present invention will become apparent from the following detailed description of the invention.

DETAILED DESCRIPTION OF THE INVENTION

The term "vaccine" as used herein means any antigenic preparation dosage form administered with the object of stimulating the recipients specific immune define mechanisms in respect of given pathogenic or toxic agents. Generally vaccine dosages contain (a) inactivated antigens such as those used to vaccinate for typhoid and cholera, (b) live attenuated antigens such as those used to vaccinate for yellow fever and tuberculosis, (c) antigenic extracts of specific antigens and (d) toxoids. The term "adjuvant" as used herein means any substance which when administered in conjunction with an antigen heighthens, or affects qualitatively, the immune response to that antigen. Adjuvants are commonly administered with the object of increasing the immunogenicity of an antigen in order to stimulate a higher rate of antibody formation for a more vigorous response in cell mediated immunity with respect to that antigen.

The compounds of the present invention can be incorporated into a vaccine useful for vaccinating vertebrates. A vaccine dosage suitable for immunizing a vertebrate against any common disease and an adjuvant dosage comprising the RAL derivatives of the present invention are administered in conjunction. The adjuvant is administered independently of the vaccine prior to, contemporaneously with, or subsequent to the vaccine administration. Alternatively, the RAL derivative adjuvants can be mixed with the vaccine dosage to form a single dosage containing the vaccine dosage and the adjuvant dosage.

Immunostimulating RAL derivatives of the present invention are zearalenone, zearalanone, zearalene, zearalane, zearalenol, zearalanol, and dideoxyzearalane.

Zearalenone is prepared by cultivating the organism *Gibberella zeae* (Gordon) on deposit at the Northern Utilization Research and Developed Division of the U.S. Department of Agriculture under the number NRRL-2830 according to the method disclosed in U.S. Pat. No. 3,196,019, incorporated herein by reference.

Zearalanone is prepared by reducing the macrocylic ring double bond of zearalenone according to the method disclosed in U.S. Pat. No. 3,239,354, incorporated herein by reference.

Zearalene and Zearalane are prepared by (1) removing the ring ketone group of zearalenone and (2) reducing the ring double bond of zearalene according to the method disclosed in U.S. Pat. No. 3,239,341, incorporated herein by reference.

Zearalenol is prepared by reducing the zearalenone ring ketone group to form an alcohol according to the method disclosed in U.S. Pat. No. 3,239,348, incorporated herein by reference.

Zearalanol is produced by reducing the zearalenol ring double bond according to the method disclosed in U.S. Pat. No. 3,239,345, incorporated herein by reference.

Dideoxyzearalane is prepared by removing the hydroxyl groups from zearalane according to the method disclosed in U.S. Pat. No. 3,453,367, incorporated herein by reference.

The RAL derivatives according to the present invention are administered to vertebrates with poorly functioning immune systems typically caused by malnutrition, trauma, infection, or diseases, but preferably are administered to healthier vertebrates to stimulate the immune system and increase resistance to infection and disease and increase the recovery time from injury or other trauma. The RAL derivatives according to the present invention stimulate the proliferation of macrophages in the immune system and increase the amount of $O_2{}^-$ produced by the macrophages. The RAL derivatives of the present invention also stimulate the immune system to increase the survivability of test vertebrates presented with lethal bacteria challenge.

Typical vertebrates having immune systems stimulated by the RAL derivatives of the present invention are humans, poultry and livestock such as cattle, horses, sheep, swine, chickens, turkeys, ducks, geese, pheasants, quail, and the like.

The amount of RAL derivatives of the present invention administered may vary depending upon the particular type of vertebrate, the maturity of the vertebrate, and the size of the vertebrate. Generally, the RAL derivatives according to the present invention are administered to the vertebrate in dosages from 1–20 mg/kg of body weight, preferably from 5–15 mg/kg of body weight, and most preferably from 9–12 mg/kg of body weight.

The RAL derivatives of the present invention can be administered as the compound or as a pharmaceutically acceptable salt of the compound, alone, in combination, or in combination with pharmaceutically acceptable carriers, diluents, and vehicles. The carrier can be an antibiotic, other immune stimulating agent, an inert carrier, and the like. More preferably, the RAL derivatives of the present invention are mixed with a pharmaceutically acceptable carrier to form a composition which allows for easy dosage preparation.

The RAL derivatives of the present invention can be administered to the vertebrate in any acceptable manner including orally, by injection, using an implant, and the like. Oral administration includes administering the RAL derivatives of the present invention in tablets, suspensions, implants, solutions, emulsions, capsules, powders, syrups, water compositions, feed compositions, and the like. Injections and implants are preferred because they permit percise control of the timing and dosage levels used for administration, with injections being most preferred. The RAL derivatives of the present invention are preferably administered parenterally. Such administration may be by intravenous or intramuscular injection, intraperitoneal injection, or subcutaneous implant.

When given by injection, the RAL derivatives of the present invention can be administered to the vertebrates with any biocompatable and RAL derivative compatable carrier such as various vehicles, adjuvants, additives, and diluents to achieve a composition usable as a dosage form. The RAL derivatives of the present invention are added to the carrier in amounts sufficient to supply from about 1–20 mg/kg of body weight to the vertebrate when injected. Preferably, the RAL derivatives of the present invention are added to a oil vehicle in amounts sufficent to supply from about 9–12 mg/kg of body weight.

Aqueous vehicles such as water having no nonvolatile pyrogens, sterile water, and bacteriostatic water are also suitable to form injectable RAL derivative compositions. In addition to these forms of water, several other aqueous vehicles can be used. These include isotonic injection compositions that can be sterilized such as sodium chloride, Ringer's, dextrose, dextrose and sodium chloride, and lactated Ringer's. Addition of water-miscible solvents, such as methanol, ethanol, or propylene glycol generally increases solubility and stability of the RAL derivatives in these vehicles.

Nonaqueous vehicles such as cottonseed oil, sesame oil, or peanut oil and esters such as isopropyl myristate may also be used as solvent systems for RAL derivative compositions. Additionally various additives which enhance the stability, sterility, and isotonicity of the composition including antimicrobial preservatives, antioxidants, chelating agents, and buffers can be added. Any vehicle, diluent, or additive used would, however, have to be compatible with the RAL derivatives of the present invention. Preferably the RAL derivative is administered with a sesame oil vehicle.

The RAL derivatives according to the present invention can be administered to the vertebrate in the form of a slow-release subcutaneous implant which is inserted beneath the skin of the vertebrate, preferably ion the ear for large animals The implant can take the form of a pellet which slowly dissolves after being implanted in the vertebrate or a biocompatible and RAL derivative compatible delivery module well known to those skilled in the art. Such well known dosage forms are designed such that the active ingredients are slowly released over a period of several days to several weeks. The implant is designed to deliver from about 1–20 mg/kg of body weight/day, preferably from about 5–15 mg/kg of body weight/day, and most preferably from about 9–12 mg/kg of body weight/day to the vertebrate.

The RAL derivatives according to the present invention can be administered orally to the vertebrate. For example, the RAL derivatives of the present invention can be blended with ordinary feed compositions or added to drinking water in amounts sufficient to stimulate the vertebrate's immune system. When the RAL derivatives of the present invention are to be administered in feeds, an vertebrate feed composition may be prepared containing the usual nutritionally-balanced feed containing quantities of carbohydrates, proteins, vitamins and minerals, together with the RAL derivatives in accordance with the present invention. Some of the usual dietary elements included in vertebrate feed compositions are grains, such as ground grain and grain byproducts, animal protein substances, such as those found in fish meal and meat scraps, vegetable proteins, like soybean oil meal or peanut oil meal; vitamins and vitamin-containing materials, e.g., vitamin A and D mixtures, riboflavin supplements and other vitamin B complex members; and bone meal and limestone to provide minerals. A type of conventional feed material for use with cattle includes alfalfa hay and ground corncobs together with supplementary vitamins and vitamin-containing substances if desired. The RAL derivatives according to the present invention are admixed with the feed in amounts sufficient to supply from about 1–20 grams/kg body weight, typically 15–120 grams/ton of feed, to the vertebrate.

The RAL derivatives of the present invention are useful for stimulating the immune system of vertebrates, particularly livestock and poultry, which are susceptible to or suffering from various infections and diseases such as shipping fever, influenza, hoof and mouth disease, and the like. Additionally, the RAL derivatives are useful for stimulating the immune system of vertebrates recovering from surgery, injury, stress, infection, or other trauma. Stimulating the immune system improves the chance of survival and recovery time and increases the resistance to infections and disease.

The RAL derivatives are also useful as injectable vaccine adjuvants when used in conjunction with vaccines such as, but not limited to, those for influenza, hoof and mouth disease, hepatitis, rabies, distemper, meningitis, cholera, enteritis, diphtheria, measles, mumps, and the like. The compounds may be incorporated in the dose of the vaccine in an amount from about 1–20 milligrams per dose of vaccine, preferably with a pharmaceutically-acceptable vehicle or carrier such as a fat or lipid emulsion or glycerol. The vertebrate is vaccinated by administering the vaccine-adjuvant dose to the vertebrate in the manner conventional for the particular vaccine, generally as a single dose administered subcutaneously or intramuscularly. Alternatively, the vertebrate is vaccinated by administering RAL derivatives independently of the vaccine prior to, contemporaneously with, or subsquent to vaccine administration, preferably about 8–24 hours prior to administration of the vaccine. The RAL derivatives stimulate the immune system thereby improving the response to the vaccine. Typically, vaccines known in the art are formulations of antigens that stimulate the vertibrate immune system, typically formulations of attenuated viruses, inactivated viruses, killed bacteria, or small doses of live bacteria, viruses, or other pathogens.

The invention having been generally described, the following examples are given as particular embodiments of the invention and to demonstrate the practice and advantages thereof. It is understood that the examples are given by way of illustration and are not intended to limit the specification or the claims to follow in any manner.

IN VIVO EXPERIMENTAL PROCEDURE

The immunostimulating compounds and controls were administered via intraperitoneal injection to intact Swiss Webster (S/W) mice, on day -3, -2, and -1 before intraperitoneal challenge with $2-5 \times 10^5$ viable *Salmonella typhimurium*. Typically, ten to twenty mice per group plus an additional ten mice for macrophage (M$\phi$) activation studies were used. The percent survival rate versus time was calculated and used to gauge the effectiveness of these immunostimulating compounds.

EXAMPLE 1

Zearalane and dideoxyzearalane in a sesame oil vehicle were tested for immunostimulating activity by testing the anti-infective activity using the above procedure. The results, shown in Table 1, indicate that Zearalane delays mortality and morbidity and enhances survival as compared to the controls.

EXAMPLE 2

Zearalane and dideoxyzearalane in a sesame oil vehicle were tested for immunostimulating activity by testing the anti-infective activity using additional controls, saline and tetracycline. The results, shown in Table 2, indicate an decreased mortality and morbidity and increased survival rate when compared to the controls. Additionally, Table 2 shows that the positive effects are not attributable solely to the sesame oil vehicle, saline, or tetracycline.

EXAMPLE 3

Zearalane in a sesame oil vehicle was tested using the above procedure at varying dosages. Results, shown in Table 3, indicate that zearalane gives a positive effect on survivability in dosages as low as 0.3 mg/kg over the controls.

EXAMPLE 4

Zearalane and zearalanol are compared to various estrogenic compounds, particularly estradiol and diethylstilbesterol, to test their immunostimulating properties. The results, shown in Table 4, indicate that the RAL derivatives zearalane and zearalanol possess immunostimulating properties whereas the DES and estradiol controls do not possess immunostimulating properties. Zearalane in a $H_2O$ vehicle (Hanks buffer) is particularly active in vivo when applied in an aqueous buffer.

IN VITRO EXPERIMENTAL PROCEDURE

Chemicals and Reagents

The stock solution of phorbol myristate acetate (PMA) (Consolidated Midland Corp., Brewster, NY) was made in dimethyl sulfoxide (DMSO), and aliquots were delivered directly into the reaction mixture for the assay of $O_2^-$ released. The concentration of DSMO present in the assay mixture was less than 1% and had no detectable effect on the response of the $M\phi$. Superoxide dismutase (SOD) from bovine erythrocytes was purchased from Diagnostic Data Inc., Mountain View, CA. Ferricytochrome c (horse heart, Type III) was obtained from Sigma Chemical Co., St. Louis, MO.

Macrophage Harvest and Monolayer Culture

Resident peritoneal $M\phi$ were aspirated from the peritoneal cavity of mice in Hank's balanced salt solution (HBSS) without phenol red. They were seeded into 35-mm petri dishes ($2 \times 10^6$ $M\phi$/dish) containing DMEM medium (M.A. Bioproducts) supplemented with 5% heat-inactivated fetal bovine serum (Hyclone), 2 mM L-glutamine (Flow), and 100 units/ml of penicillin and 100 $\mu$/ml streptomycin. After 2 hours of incubation in 5 percent $CO_2$ at 37° C., nonadherent cells were washed out, and the monolayers were incubated in fresh medium for 24 hours which time the $O_2^-$ assay was done. The adherent cell population is greater than 98 percent (%) α-naphthyl esterase-positive indicating that the $M\phi$'s had been suscessfully harvested. $M\phi$ viability (95 to 98%) was determined using the trypan blue exclusion test. In vivo activated peritoneal $M\phi$ were harvested from mice that had been treated three days prior with RAL derivatives.

SUPEROXIDE ANION ASSAY

Superoxide anion ($O_2^-$) was assayed spectrophotometrically by measuring the SOD-inhibitable reduction of cytochrome c. $M\phi$ monolayers were washed twice with HBSS without phenol red and were treated with a 2-ml assay mixture containng 0.08 mM cytochrome c in HBSS without phenol red and with either 0.5 $\mu$g/ml PMA, 0.1 ml suspensions of the *Salmonella typhimurium* cultures (10% transmittance at 600 nm), or 100 $\mu$l of opsonized zymosan (Packard). Under these conditions, very similar phagocytic indexes were obtained with the different strains of S. typhimurium studied or opsonized zymosan. For each determination, a matched assay mixture contained, in addition to the above SOD at a final concentration of 50 $\mu$g/ml. The plates were reincubated at 37° C. in 5% $CO_2$ for varying periods up to 5 hours, the assay mixtures were filter sterilized (0.2 $\mu$m membrane filters; Millipore Corp. Bedford, MA) and the absorbance was read at 550 nm in a Cary 219 stectrophotometer with 1 nm spectral band width. The absorbance of the sample containing SOD was subtracted from the sample without SOD, and this difference in cytochrome c reduction, equivalent to the amount $O_2^-$ released, was calculated using $\epsilon_{550nm} = 21,000$ $m^{-1}cm^{-1}$. After removing the assay mixture, the culture was washed twice with HBSS and the protein content was determined using the procedure of Lowry with bovine serum albumin as the standard.

EXAMPLE 5

Ten mice from each Treatment Group from Example 1 were tested using the above procedure for in vivo $M\phi$ activating activity. The results, shown in Table 5, indicate that zearalane is a potent murine peritoneal macrophage activating substance in vivo, especially when compared to the sesame oil negative control. The high activity of $O_2^-$ released from the zearalane treated mice corresponds to the level of increased protection seen in mice challenged with *S. typhimurium* over the three (3) day period.

EXAMPLE 6

Ten mice from each Treatment Group from Example 2 were tested using the above procedure for in vivo $M\phi$ activating activity. The results, shown in Table 6, indicate that zearalane treated mice released high levels of $O_2^-$ upon PMA (soluble) or live *S.typhimurium* (particulate) stimulation in vitro. The high levels of $O_2^-$ indicate considerable in vivo murine peritoneal $M\phi$ activation after three (3) consecutive days administration.

EXAMPLE 7

Ten mice from each Treatment Group from Example 3 were tested using the above procedure for in vivo $M\phi$ activating activity. The results, shown in Table 7, indicate that zearalane can activate murine peritoneal $M\phi$ in vivo in a dose dependent fashion upon opsonized zymosan stimulation.

EXAMPLE 8

Ten mice from each Treatment Group from Example 4 were tested using the above procedure for in vivo $M\phi$ activating activity. The results, shown in Table 8, indicate that zearalane, when administered in either an oil or aqueous vehicle, can activate murine peritoneal $M\phi$ by stimulating increased amounts of $O_2^-$ upon opsonized zymosan stimulation. Estrogenic compounds Estradiol and Diethyl stilbestrol had little in vivo $M\phi$ activating effects at the same dose as RAL derivatives.

EXAMPLE 9

Zearalane and dideoxyzearalane were tested at different doses to determine what level was needed to activate murine peritoneal $M\phi$ in vitro. Results, as shown in Table 9, indicate that zearalane is able to activate $M\phi$ in vitro optimally at a concentration of 500 ng/ml, upon both soluble (PMA) and particulate (opsonized zymonsan) stimulus. Dideoxyzearalane can activate murine peritoneal $M\phi$ at similar concentrations. although at much smaller levels (upon opsonized zymosan stimulus).

EXAMPLE 10

Zearalane and dideoxyzearalane were tested at a dose of 500ng/ml to see if murine alvealar M$\phi$ could be activated in vitro. Results, as shown in Table 10, indicate that zearalane can stimulate large amounts of $O_2^-$ from a subpopulation of cells distant from the peritoneal cavity of mice.

Obviously many modifications and variations of the present invention are possible in light of the above teachings. It is therefore to be understood that within the scope of the appended claims the invention may be practiced otherwise than as specifically described.

TABLE 1

Anti-infective Activity of Zearalane in Mice

| Treatment Group | Dose ($\mu$g/Mouse/Day)[a] | Total Dose (mg/kg) | % Survival Trials 1 and 2 Day 1 | Day 2 | Day 3 |
|---|---|---|---|---|---|
| Zearalane | 60 | 9.0 | 90[b] (95)[c] | 90[b] (80)[c] | 40[b] (70)[c] |
| Dideoxyzearalane | 90 | 13.5 | 90 (70) | 50 (55) | 20 (45) |
| Sesame Oil Vehicle (Negative Control) | — | — | 50 (65) | 10 (25) | 10 (15) |

[a]Test compounds were administered via intraperitoneal injection on day -3, -2, and -1 before intraperitoneal challenge with *Salmonella typhimurium*.
[b]Challenge dose = 4 × 10$^5$cells/mouse.
[c]Challenge dose = 1 × 10$^5$cells/mouse.

TABLE 2

Anti-infective Activity of Zearalane and Dideoxyzearalane in Mice

| Treatment Group | Dose ($\mu$g/ Mouse/Day)[a] | Total Dose (mg/kg) | Number of Survivors/20 Mice Days Post Challenge 1 | 2 | 3 | 4 |
|---|---|---|---|---|---|---|
| Zearalane | 60 | 9.0 | 19 | 16 | 14 | 13 |
| Dideoxyzearalane | 90 | 13.5 | 14 | 11 | 9 | 8 |
| Saline Vehicle (Negative Control) | — | — | 4 | 0 | 0 | 0 |
| Sesame Oil Vehicle (Negative Control) | — | — | 13 | 5 | 3 | 2 |
| Tetracycline in Saline (antibiotic positive control) | 500 | 75.0 | 18 | 14 | 10 | 10 |

[a]Test compounds were administered via intraperitoneal injection on day -3, -2, and -1 before intraperitoneal challenge with 3 × 10$^5$ cells of *Salmonella typhimurium*.

TABLE 3

Dose Titration of Zearalane in Mice

| Treatment Group | Dose ($\mu$g/ Mouse/Day) | Total Dose (mg/kg) | Number of Survivors/10 Mice Days Post Challenge 1 | 2 | 3 | 4 | 5 |
|---|---|---|---|---|---|---|---|
| Zearalane | 2 | 0.3 | 10 | 9 | 8 | 7 | 2 |
| Zearalane | 10 | 1.5 | 10 | 7 | 7 | 4 | 2 |
| Zearalane | 30 | 4.5 | 9 | 8 | 8 | 5 | 2 |
| Zearalane | 60 | 9.0 | 10 | 10 | 9 | 4 | 2 |
| Sesame Oil Vehicle (Negative Control) | 0.1 ml | 0.3 ml | 10 | 9 | 6 | 4 | 2 |
| Saline Vehicle | 0.1 ml | 0.3 ml | 5 | 2 | 1 | 1 | 1 |

TABLE 4

Immune Stimulant Screening

| Treatment Group | Dose ($\mu$g/ Mouse/Day)[a] | Total Dose (mg/kg) | Number of Survivors/10 Mice Days Post Challenge 1 | 2 | 3 | 4 | 5 | 6 | 7 |
|---|---|---|---|---|---|---|---|---|---|
| Diethyl Stilbesterol (in Sesame Oil) | 60 | 9.0 | 8 | 5 | 2 | 2 | 2 | 0 | 0 |
| Estradiol (in Sesame Oil) | 60 | 9.0 | 8 | 6 | 5 | 3 | 0 | 0 | 0 |
| Zearalanol (in Sesame Oil) | 60 | 9.0 | 7 | 4 | 4 | 2 | 0 | 0 | 0 |
| Zearalane (in Sesame Oil) | 60 | 9.0 | 10 | 6 | 5 | 3 | 2 | 0 | 0 |
| Dideoxyzearalane (in Sesame Oil) | 90 | 13.5 | 8 | 7 | 7 | 4 | 2 | 0 | 0 |
| Sesame Oil Vehicle (Negative Control) | 0.1 ml | 0.3 ml | 9 | 7 | 7 | 6 | 3 | 1 | 1 |
| Zearalane in HBSS | 60 | 9.0 | 10 | 10 | 9 | 9 | 8 | 1 | 1 |
| HBSS | 0.1 ml | 0.3 ml | 8 | 6 | 3 | 3 | 3 | 2 | 2 |

TABLE 4-continued

Immune Stimulant Screening

| Treatment Group | Dose (μg/ Mouse/Day)[a] | Total Dose (mg/kg) | Number of Survivors/10 Mice Days Post Challenge | | | | | | |
|---|---|---|---|---|---|---|---|---|---|
| | | | 1 | 2 | 3 | 4 | 5 | 6 | 7 |
| (Negative Control) | | | | | | | | | |

[a]Test compounds were administered via intraperitoneal injection on day -3, -2 and -1 before intraperitoneal challenge with *Salmonella typhimurium* at a dose of 2-3 × $10^5$ cell/mouse.
[b]Challenge dose = 1.5 × $10^5$ cells/mouse.
[c]HBSS is Hanks Balanced Salt Solution

TABLE 5

Superoxide Anion ($O_2^-$) Release From Murine Peritoneal Macrophages (MØ) Activated *In Vivo* with RAL Derivatives

| Treatment Group | Dose[a] (μg/mouse/day) | Total Dose (mg/kg) | $O_2^-$ Released (nmol/hr/mg protein)[b] |
|---|---|---|---|
| Zearalane | 60.0 | 9.0 | 580.0 ± 46.9 (n = 10)[c] |
| Dideoxyzearalane | 90.0 | 13.5 | 350.0 ± 60.2 (n = 8) |
| Sesame Oil Vehicle (Negative Control) | — | — | 245.0 ± 53.5 (n = 12) |

[a]Test compounds were administered via intraperitoneal injection on 3 consecutive days before intraperitoneal challenge with 4 × $10^5$ viable cells of *Salmonella typhimurium* ATCC 82-4728. MØ were harvested at Day ) of injection.
[b]Opsonized Zymosan was used as stimulus. MØ are plated at 2.0 × $10^{+6}$ cells/35 mm dish in 5% $CO_2$ and 100% humidity. MØ from infected animals released 60 ± 18 nmol of $O_2^-$/hr/mg protein in response to Opsonized Zymosan (n = 4). For each determination, a matched assay mixture containing Superoxide Dismutase (SOD) at a final concentration of 50 μg/ml was used.
[c]Data are from 5 individual experiments, Mean ± S.E. (n = 8 − 12).

TABLE 6

Superoxide Anion ($O_2^-$) Release from Murine Peritoneal Macrophages Activated *In Vivo* with RAL Derivatives

| Treatment Group | Dose[a] (μg/mouse/day) | Total Dose (mg/kg) | $O_3^-$ Released (nmol/hr/mg protein[b]) Stimulus | |
|---|---|---|---|---|
| | | | PMA | Live *S. typhimurium* |
| Zearalane | 60.0 | 9.0 | 362.0 ± 55.3 (n = 6) | 380.2 ± 4.5 (n = 4) |
| Dideoxyzearalane | 90.0 | 13.5 | 52.3 ± 20.4 (n = 4) | — |
| Saline Vehicle (Negative Control) | — | — | 87.3 ± 14.9 (n = 5) | 2.1 ± 0.1 (n = 5) |
| Sesame Oil Vehicle (Negative Control) | — | — | 72.3 ± 15.0 (n = 8) | 10.5 ± 8.2 (n = 4) |
| Tetracycline in Saline | 500.0 | 75.5 | 206.7 ± 45.0 (n = 6) | 99.9 ± 24.3 (n = 5) |

[a]Test compounds were administered via intraperitoneal injection on 3 consecutive days before intraperitoneal challenge with 3 × $10^5$ viable cells of *Salmonella typhimurium* ATCC 82-4728. MØ's were harvested at Day 0 of infection.
[b]Two stimuli were used: Phorbol Myristate Acetate (PMA; 0.5 μg/ml) and live *Salmonella typhimurium* (opsonized). MØ are plated at 2.0 × $10^6$ cells/35 mm dish in 5% $CO_2$ at 37° C. and 100% humidity. MØ cells from untreated control mice stimulated with PMA or *Salmonella typhimurium* released <50 nmol/hr/mg. For each determination, a matched assay mixture containing Superoxide Dismutase (SOD) at a final concentration of 50 μg/mlwas used.
[c]Data are from two individual experiments, Mean ± S.E. (n = 4 − 8).

TABLE 7

Dose-Dependent Activation of Murine Peritoneal Macrophages (MØ) Activated *In Vivo* with RAL Zearalane

| Treatment Group | Dose (μg/mouse/day) | Total Dose (mg/kg) | $O_2^-$ Released (nmol/hr/mg protein)[b] |
|---|---|---|---|
| Zearalane | 2.0 | 0.3 | 140.5 ± 3.7 |
| Zearalane | 10.0 | 1.5 | 160.5 ± 78.0 |
| Zearalane | 30.0 | 4.5 | 201.5 ± 27.2 |
| Zearalane | 60.0 | 9.0 | 315.0 ± 28.4 (n = 6) |
| Sesame Oil Vehicle (Negative Control) | — | — | 93.3 ± 5.3 (n = 5) |
| Saline (Negative Control) | — | — | 59.2 ± 5.0 (n = 5) |

[a]Test compounds were administered via intraperitoneal injection on 3 consecutive days before intraperitoneal challenge with 3 × $10^5$ viable cells of *Salmonella typhimurium* ATCC 82-4728. MØ cells were harvested at Day 0 of infection.
[b]Opsonized Zymonsan was used as stimulus. MØ are plated at 2.0 × $10^6$ cells/35 mm dish in 5% $CO_2$ and 100% humidity. For each determination, a matched assay mixture containing Superoxide Dismutase (SOD) at a final concentration of 50 μg/ml.
[c]Data are from 2 individual experiments, Mean ± S.E. n = 3 −6).

TABLE 8

Superoxide Anion ($O_2^-$) Released From Murine Peritoneal Macrophages (MØ) Activated *In Vivo* With RAL Derivatives

| Treatment Group | Dose [a] (μg/mouse/day) | Total Dose (mg/kg) | $O_2^-$ Released (nmol/hr/mg protein)[b] |
|---|---|---|---|
| Diethyl Stibesterol (in Sesame Oil) | 60.0 | 9.0 | 8.4 ± 1.41[c] (n = 4) |
| Estradiol (in Sesame Oil) | 60.0 | 9.0 | 2.5 ± 0.6 (n = 6) |
| Zearalanol (in Sesame Oil) | 60.0 | 9.0 | 112.4 ± 5.0 (n = 3) |
| Dideoxyzearalane (in Sesame Oil) | 90.0 | 13.5 | 125.0 ± 10.0 (n = 3) |
| Zearalane (in Sesame Oil) | 60.0 | 9.0 | 301.7 ± 34.5 (n = 5) |
| Zearalane in HBSS | 60.0 | 9.0 | 819.1 ± 248.6 (n = 5) |
| Sesame Oil Vehicle (Negative Control) | — | — | 42.6 ± 10.0 (n = 3) |
| HBSS Vehicle (Negative Control) | — | — | 59.2 ± 28.4 (n = 3) |

[a] Test compounds were administered via intraperitoneal injection on 3 consecutive days before intraperitoneal challenge with 4 × 10+5 viable cells of *Salmonella typhimurium* ATCC 82-4728. MØ were harvested at day 0 of infection.
[b] Opsonized Zymosan was used as stimulus. MØ are plated at 2.0 × 10+6 cells/35 mm dish in 5% $CO_2$ and 100% humidity. MØ from control animals (untreated) released 60 ± 18 nmol of $O_2^-$/hr/mg protein in response to Opsonized Zymosan (n = 4). For each determination, a matched assay mixture containing Superoxide Dismutase (SOD) at a final concentration of 50 μg/ml was used.
[c] Data are from 3 individual experiments, Mean ± S.E. (n = 3 − 6).

TABLE 9

Dose-Dependent Activation of Murine Peritoneal Macrophages (MØ) Activated *In Vivo* with RAL Derivatives

| RAL | Stimulus | RAL Concentration (ng/ml) | | | | |
|---|---|---|---|---|---|---|
| | | 0.001 | 0.01 | 0.1 | 1.0 | 10.0 |
| | | Superoxide Anion ($O_2^-$) Released (nmol/hr/mg protein)[a] | | | | |
| Zearalane | Opsonized Zymosan | 110 ± 20 | 1190 ± 237 | 1507 ± 0.0 | 1932 ± 178 | 2217 ± 159 |
| Zearalane | PMA (0.5 μg/ml) | — | 224.5 ± 0.9 | 214.9 ± 23.4 | 205.0 ± 24.1 | 163.1 ± 22.1 |
| Dideoxy-Zearalane | Opsonized Zymosan | 2.8 ± 0.3 | — | 39.5 ± 3.9 | 49.7 ± 1.2 | 140.0 ± 6.3 |
| Dideoxy-Zearalane | PMA (0.5 μg/ml) | — | 7.9 ± 4.6 | — | 48 ± 10 | 99 ± 17 |

| RAL | Stimulus | RAL Concentration (ng/ml) | | | | |
|---|---|---|---|---|---|---|
| | | 100.0 | 250.0 | 500.0 | 1000.0 | 5000.0 |
| | | Superoxide Anion ($O_2^-$) Released (nmol/hr/mg protein)[a] | | | | |
| Zearalane | Opsonized Zymosan | 2693 ± 189 | 2176 ± 287 | 2493 ± 578 | 1970 ± 594 | 491 ± 275 |
| Zearalane | PMA (0.5 μg/ml) | 185.1 ± 15.6 | 284.9 ± 19.7 | — | 393.3 ± 19.3 | 215.4 ± 12.6 |
| Dideoxy-Zearalane | Opsonized Zymosan | 503.9 ± 8.8 | — | 695.7 ± 5.8 | 658.5 ± 55.6 | 590.9 ± 61.4 |
| Dideoxy-Zearalane | PMA (0.5 μg/ml) | 263 ± 46.8 | — | 234 ± 8.5 | 134 ± 11.5 | — |

[a] MØ were plated at 2.0 × 10⁶ cells/35 mm dish in 5% $CO_2$ and 100% humidity. For each determination, a matched assay mixture containing Superoxide Dismutase (SOD) at a final concentration of 50 μg/ml was used. Data are from 1-4 separate experiments, Mean ± S.E. (n = 3 − 8).

TABLE 10

Superoxide Anion ($O_2^-$) Release from Murine Alveolar Macrophages (MØ) Activated *In Vivo* with RAL Derivatives

| RAL Derivative | Dose | $O_2^-$ Released[a] (nmol/hr/mg protein) |
|---|---|---|
| Control (unstimulated) | — | 68.1 ± 15.1 (n = 4) |
| Zearalane | 500 ng/ml | 552.3 ± 52.1 (n = 6) |
| Dideoxyzearalane | 500 ng/ml | 100.0 ± 10.0 (n = 4) |

[a] Opsonized Zymosan was used as stimulus. MØ were plated at 2.0 × 10⁶ cells/35 mm dish in 5% $CO_2$ and 100% humidity. For each determination, a matched assay mixture containing Superoxide Dismutase (SOD) at a final concentration of 50 μg/ml was used. Data are from 2 experiments, Mean ± S.E. (n = 4 − 6).

What is claimed is:

1. A method for non-specifically stimulating the vertebrate immune system comprising the step of: administering to said vertebrate from about 1-20 mg/kg of body weight of at least one compound selected from the group consisting of zearalenone, zearalanone, zearalene, zearalane, zearalenol, zearalanol, and dideoxyzearalane.

2. The method of claim 1 wherein said compound is zearalane.

3. The method of claim 1 wherein said compound is administered orally, said oral method selected from the group consisting of administering said compound to said vertebrates in tablets, suspensions, solutions, emulsions, capsules, powders, syrups, drinking water compositions, and feed compositions.

4. The method of claim 1 wherein said compound is administered in a feed composition, said feed composition further comprising:

a nutritionally balanced feed; and
from about 15-125 grams per ton of feed of at least one of said compounds admixed with said feed.

5. The method of claim 1 wherein said compound is administered by injecting a composition, said composition further comprising:
a biocompatible and RAL derivative compatable vehicle; and
an immune stimulating amount of at least one of said compounds admixed with said composition.

6. The method of claim 5 wherein said vehicle is an oil vehicle.

7. The method of claim 1 wherein said compound is administered using an implant, said implant further comprising:
a biocompatible and RAL derivative compatable implant material; and
an immune stimulating amount of at least one of said compounds admixed with said implant material.

8. A composition suitable for non-specifically stimulating the vertebrate immune system comprising:
at least one compound selected from the group consisting of zearalenone, zearalanone, zearalane, zearalene, and zearalenol, zearalanol, and dideoxyzearalane, wherein the amount of said compound in said composition is sufficient to supply from about 1-20 mg/kg body weight to said vertebrate; and
an inert pharmaceutical carrier.

9. The composition of claim 8 wherein said compound is zearalane.

10. The composition of claim 8 wherein said composition is an injectable composition suitable for stimulating the immune system in vertebrates further comprising:
a biocompatible and RAL derivative compatable vehicle; and
an immune stimulating amount of at least one of said compounds admixed with said vehicle.

11. The composition of claim 10 wherein said vehicle is an oil vehicle.

12. The composition of claim 8 wherein said composition is a feed composition suitable for stimulating the immune system in vertebrates further comprising:
a nutritionally balanced feed; and
from about 15-125 grams per ton of feed of at least one of said compounds admixed with said feed.

13. The composition of claim 8 wherein said composition is an implant suitable for stimulating the immune system in vertebrates further comprising:
a biocompatible implant material; and
a immune stimulating amount of at least one of said compounds admixed with said implant material.

14. A method for enhancing the efficacy of a vaccine administered to a vertebrate comprising:
administering in conjunction, a vaccine; and
from about 1-20 mg/kg body weight of an adjuvant comprising at least one compound selected from the group consisting of zearalenone, zearalanone, zearalene, zearalane, zearalenol, zearalanol, and dideoxyzearalane.

15. The method of claim 14 wherein said compound is zearalane.

16. The method of claim 14 wherein said adjuvant is administered independently of the vaccine prior to, contemporaneously with, or subsequent to said vaccine administration.

17. The method of claim 14 wherein said adjuvant is incorporated in the dose of said vaccine.

18. The method of claim 14 wherein said adjuvant is incorporated in the dose of said vaccine in an amount from about 1-20 milligrams per dose of vaccine.

* * * * *

UNITED STATES PATENT AND TRADEMARK OFFICE
CERTIFICATE OF CORRECTION

PATENT NO. : 4,842,862

DATED : June 27, 1989

INVENTOR(S) : M. J. Jacobs, C. K. Edwards, III and P. M. Keith

It is certified that error appears in the above-identified patent and that said Letters Patent is hereby corrected as shown below:

Column 1, line 57, "succeptable" should read --susceptible--
Column 2, line 52, "migitate" should read --mitigate--
Column 3, line 12, "define" should read --defense--
Column 3, line 20, "heighthens" should read --heightens--
Column 3, line 20, "qualitively" should read --qualitatively--
Column 4, line 20, "derivatives" should read --derivative--
Column 4, line 35, "More" should read --Most--
Column 4, line 47, "percise" should read --precise--
Column 4, line 56, "biocompatable" should read --biocompatible--
Column 4, line 56 & 57, "compatable" should read --compatible--
Column 5, line 23, "ion" should read --in--
Column 5, line 42, "an" should read --a--
Column 6, line 27, "vertibrate" should read --vertebrate--
Column 6, line 64, "an" should read --a--
Column 7, line 38, "($2 \times 10^6$ M$\emptyset$/dish) should read --($2 \times 10^6$ $\emptyset$M$\emptyset$/dish)--
Column 8, lines 64 & 65, "zymonsan)" should read --zymosan)--
Column 9, line 4, "alvealar" should read --aveolar--
Column 10, Table 3, Under the Heading "Treatment", line 7, "Saline Vehicle" should read
--Saline Vehicle
   (Negative Control--
Column 11, Table 5, Footnote$^a$, line 3, "Day)" should read --Day 0--
Column 11, Table 6, Heading in Columns 4 and 5, "$O_3$ - Released (nmol/hr/mg protein$^b$)" should read
--$O_2$ - Released (nmol/hr/mg protein$^b$)--

UNITED STATES PATENT AND TRADEMARK OFFICE
CERTIFICATE OF CORRECTION

PATENT NO. : 4,842,862
DATED : June 27, 1989
INVENTOR(S) : M. J. Jacobs, C. K. Edwards, III and P. M. Keith It is certified that error appears in the above-identified patent and that said Letters Patent is hereby corrected as shown below:

Column 11, Table 7, Footnote$^b$, line 1, "Zymonsan" should read --Zymosan--

Column 13, Table 8, Footnote$^a$, line 2, "4 x 10+5" should read --4 x 10$^{-5}$--

Column 13, Table 9, In the Heading, line 2, "In Vivo" should read --In Vitro--

Column 13, Table 10, In the Heading, Line 2, "In Vivo" --In Vitro--

Column 15, Claim 5, line 7, "compatable" should read --compatible--

Column 15, Claim 7, line 16, "compatable" should read --compatible--

Column 16, Claim 16, line 29, "subsquent" should read --subsequent--

Column 15, Claim 10, line 35, "compatable" should read --compatible--

Signed and Sealed this

Fourth Day of September, 1990

*Attest:*

HARRY F. MANBECK, JR.

*Attesting Officer*   *Commissioner of Patents and Trademarks*